United States Patent [19]
Menon et al.

[11] Patent Number: 5,273,024
[45] Date of Patent: Dec. 28, 1993

[54] METHOD AND APPARATUS FOR PERFORMING ENDOSCOPIC SURGERY

[75] Inventors: Jay Menon, Claremont, Calif.; Rance A. Winkler, Largo, Fla.

[73] Assignee: Linvatec Corporation, Largo, Fla.

[21] Appl. No.: 823,792

[22] Filed: Jan. 22, 1992

[51] Int. Cl.⁵ .............................................. A61B 1/00
[52] U.S. Cl. ........................................ 128/4; 128/898
[58] Field of Search .................... 128/3, 20, 17, 4, 18, 128/898; 606/167, 172, 148, 150, 170, 190, 191

[56] References Cited

U.S. PATENT DOCUMENTS

| | | | |
|---|---|---|---|
| 2,134,265 | 10/1938 | Rosenfeld | 606/172 |
| 2,575,253 | 11/1951 | Bicek | 128/3 |
| 4,432,351 | 2/1984 | Hoary | 128/3 X |
| 4,790,314 | 12/1988 | Weaver | 606/191 |
| 4,819,620 | 4/1989 | Okutsu | |
| 5,029,573 | 7/1991 | Chow | |
| 5,071,408 | 10/1991 | Ahmed | |
| 5,089,000 | 2/1992 | Agee et al. | |

FOREIGN PATENT DOCUMENTS 748057 10/1944 Fed. Rep. of Germany .......... 128/3

OTHER PUBLICATIONS

Smith+Nephew Dyonics, Inc. product brochure entitled "A Breakthrough in Carpal Tunnel Release" printed Dec. 1990, #D-1599 10M.

3M HealthCare Orthopedics Products Division, #70-2008-3888-9 (502.5) VP ©3M Oct., 1989.

Kinetix Instruments Presents AccuSharp © 1991 Kinetix.

*Primary Examiner*—Richard J. Apley
*Assistant Examiner*—Karen A. Jalbert
*Attorney, Agent, or Firm*—Gene Warzecha

[57] ABSTRACT

An endoscopic surgical procedure and instruments are disclosed for the treatment of transverse carpal ligaments and similar anatomical structures. The procedure enables the release of the carpal ligament under endoscopic control and through only a single incision. A uniquely shaped grooved cannula is provided to enable access to the carpal tunnel while also stabilizing instruments used in the procedure. The procedure involves the insertion of the cannula into the carpal tunnel through a single incision. The cannula has a longitudinal groove which is positioned to face or abut the ligament and which axially receives an endoscope through its proximal open end and obliquely receives a knife which is then positioned to cut the ligament from the side where the scope is placed.

13 Claims, 10 Drawing Sheets

METHOD AND APPARATUS FOR PERFORMING ENDOSCOPIC SURGERY

BACKGROUND OF THE INVENTION

1. Field of the Invention

This invention relates to method and apparatus for use in performing endoscopic surgical procedures. More particularly, this invention relates to a method and apparatus for performing a carpal tunnel release endoscopically.

2. Description of the Prior Art

Because of the trauma associated with open surgical procedures, efforts have been recently accelerated to develop endoscopic alternatives to all types of open surgical procedures. This invention relates to an endoscopic alternative to one such open procedure—the treatment of carpal tunnel syndrome, caused by the compression of the median nerve by the transverse carpal ligament. The treatment generally involves a procedure during which the carpal ligament is severed. While endoscopic versions of this procedure have been used in the past with varying degrees of success, continued development of endoscopic procedures to improve efficiencies and reduce patient trauma is always desirable.

Although the preferred embodiment of this invention relates to carpal ligament release, it will be understood by those skilled in the art that the method and apparatus disclosed herein may be easily adapted to other surgical procedures.

One system recently developed for the endoscopic treatment of carpal tunnel syndrome is described in U.S. Pat. No. 5,029,573 (Chow). Chow describes other prior art endoscopic carpal tunnel release procedures and claims his invention to be an improvement over the prior art in that the carpal ligament may be severed under direct viewing through an endoscope. As used herein, the term "endoscope" is intended to be generic and refers to any type of optical system used to view the interior of a patient. In the Chow procedure a cylindrical sheath, open at both ends and having a longitudinal slot in its periphery, is inserted through an incision in the wrist, under the carpal tunnel and out through an incision in the patient's palm. An endoscope is inserted in one end of the cannula and a cutting instrument is inserted in the other so that its cutting blade protrudes out of the longitudinal slot in order to cut the carpal ligament.

While the Chow procedure is undoubtedly an improvement over open surgical procedures, the necessity to use two portals, one of them being in the palm, is a disadvantage which it would be preferable to avoid. One prior art system—the Agee Inside Job ™ Carpal Tunnel Release System—has been known to provide a single portal endoscopic carpal tunnel release procedure. While avoiding some disadvantage associated with Chow's procedure and instruments, the Agee system has other disadvantages. The Agee system utilizes a cannula having a small proximal window through which a knife may be projected under the control of a trigger on a handpiece. The knife has a retrograde cutting edge and retraction of the knife cuts the carpal ligament. This type of motion has been found difficult to adequately control. Accordingly, while it is an object of this invention to produce a method and apparatus for the endoscopic treatment of carpal tunnel syndrome which avoids the necessity to create two incisions, it is also an object to produce a single portal method and apparatus which is easier to use than known single portal procedures and instruments.

An additional disadvantage associated with the Chow procedure is the relatively large number of cutting instruments required during the course of the procedure. This not only adds to the cost of the instrumentation but also adds to the time required to complete the procedure, thereby creating additional trauma for the patient. The Agee system, while having only one disposable blade assembly, has a complex, non-disposable handpiece. It is consequently another object of this invention to produce a method and apparatus for the endoscopic release of a carpal tunnel ligament using a minimum of instruments in order to simplify the procedure and minimize the amount of time required for its completion.

Another difficulty with prior art endoscopic carpal ligament release systems is that the cannula inserted under the carpal ligament is cylindrical, thereby making it hard to align the longitudinal slot or window properly and hold it in place during the cutting step. Prior art slotted cannulas have been found to rotate easily during the surgical procedure. It is extremely important that the cannula be maintained with the slot facing the ligament, even during manipulation of the scope, so that the surgeon can be assured that the slot does not face any critical features such as the median nerve. Therefore, it is another object of this invention to produce a method and apparatus which facilitates the alignment of a cannula under the carpal ligament.

It is still another object of this invention to produce an endoscopic surgical procedure and apparatus suitable for use in surgical procedures other than carpal ligament release.

It is yet another object of this invention to produce disposable instruments for use in endoscopic carpal ligament release procedures as well as other endoscopic surgical procedures.

SUMMARY OF THE INVENTION

These and other objects of the invention are achieved by the preferred embodiment hereof which is a device and method for use in an endoscopic surgical procedure which, in one preferred embodiment, is a carpal ligament release procedure. The device forming a part of the present invention is a device for use in an endoscopic surgical procedure comprising an elongated cannula closed at the distal end and open at the proximal end, the cannula provided with a longitudinal slot extending from a point adjacent the closed distal end to a point adjacent the open proximal end. The cannula has a D-shaped interior cross-section with the flat part of the D-shape lying along the rim of the longitudinal slot.

The method of the invention hereof is a method for the endoscopic treatment of a portion of the human anatomy comprising the steps of inserting an elongated slotted cannula into a body through a single incision, the cannula having a closed distal end, an open proximal end, a longitudinal slot and a D-shaped interior cross-section with the flat part of the "D" lying along the rim of the longitudinal slot; placing the longitudinal slot adjacent a work site; inserting an endoscope through the open (proximal) end of the cannula into a position to view a desired work site adjacent the longitudinal slot of the cannula inserting through the longitudinal slot, obliquely to the axis of the cannula and in front of the viewing port of the endoscope, an instrument (such as a knife) for treatment of the work site adjacent the longitudinal slot.

DESCRIPTION OF THE PREFERRED EMBODIMENT

Figure 1:
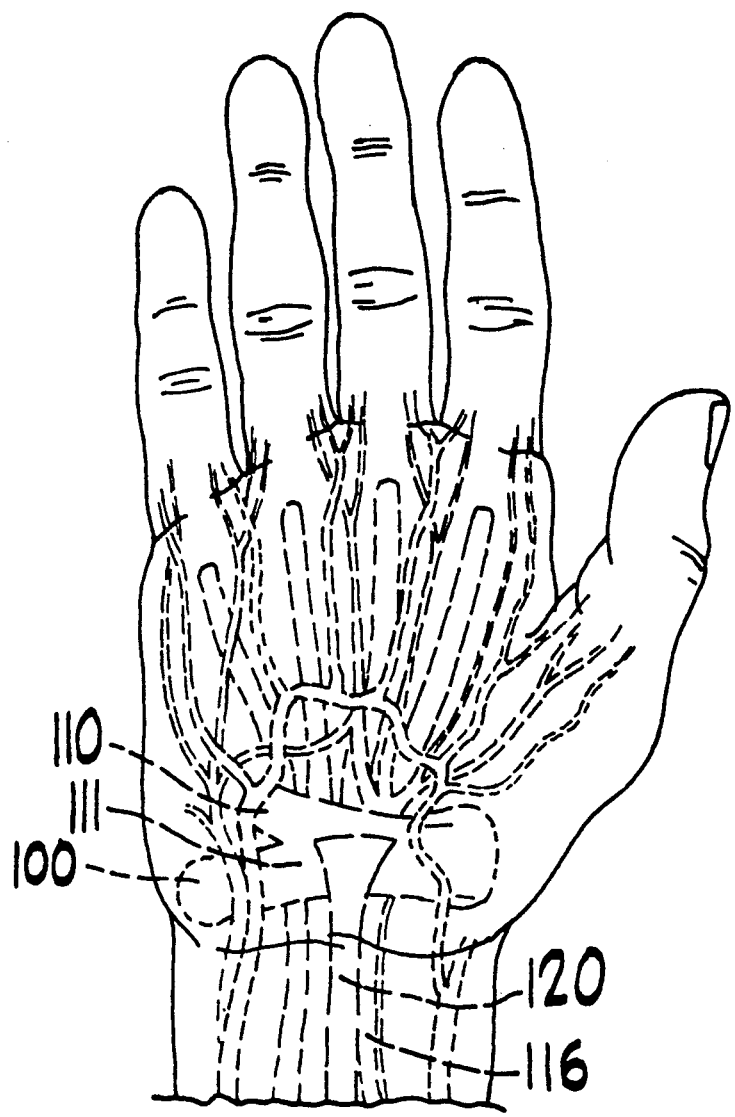
FIG. 1 is a schematic view of a human palm and wrist showing the locations of various anatomical features.

Referring to the drawings, FIGS. 1-7 and 15 show schematic representations of a human palm and wrist with various anatomical features identified, and describe various steps forming part of the invention hereof. FIGS. 8-14 show the devices which are used to perform the various method steps, some of these devices also being part of the invention hereof. An explanation of the inventive aspects of the method and devices disclosed herein is best achieved by describing the method steps with reference to the drawings and the instruments.

Figure 2:
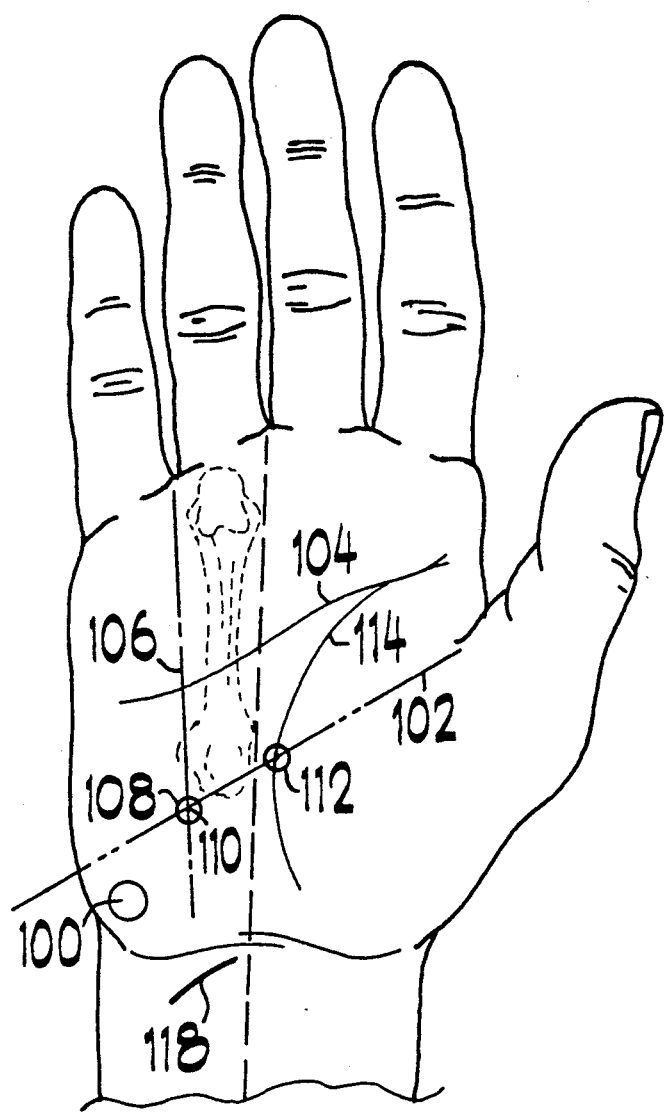
FIG. 2 is a schematic view of a human palm and wrist showing additional anatomical features and showing some of the landmarks used during the procedure described herein.
Figure 3:
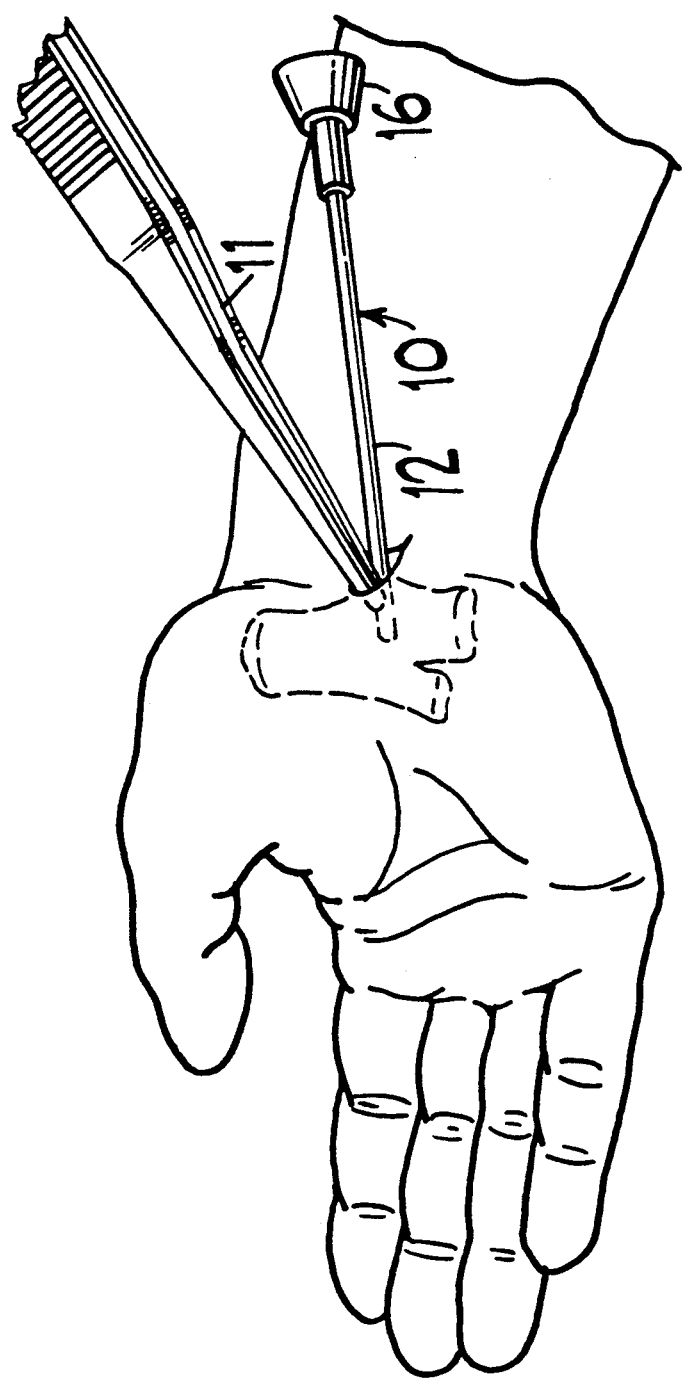
FIGS. 3, 4, 5, and 6 are schematic views of a human palm and wrist showing the positions of some of the surgical instruments during various portions of the procedure which is the subject hereof.

First, various landmarks shown in FIGS. 1 and 2 are marked. The pisiform bone is palpated and marked on the ulnar aspect of the wrist. The cardinal line of Kaplan (line 1) is drawn from the apex of the interdigital space between the thumb and the index finger towards the ulnar side of the hand parallel to the proximal palmar crease. This line passes 4-5 millimeters in front of the pisiform. A second line (line 2) is drawn as a continuation of the ulnar border of the ring finger in the proximal direction towards the wrist. This line intersects the cardinal line at a point radial and distal to the pisiform. The point of intersection of these lines corresponds to the hook of the hamate (i.e. the distal ulnar attachment of the transverse carpal ligament) and is referred to herein as point 1. One additional point of reference, point 2, is the intersection of the thenar crease with the cardinal line. The motor branch of the median nerve emerges from beneath the transverse carpal ligament and makes a recurrent course at this point. The distal border of the transverse carpal ligament will lie between points 1 and 2.

A one centimeter oblique incision is then made ulnar to the palmaris longus tendon starting at the junction of the distal wrist crease with a line drawn along the radial border of the ring finger (best seen in FIG. 2). By blunt and sharp dissection with either the instruments described below or with other, standard instruments, the transverse fibers of the antebrachial fascia of the forearm are split and the carpal tunnel is reached.

Figure 11:
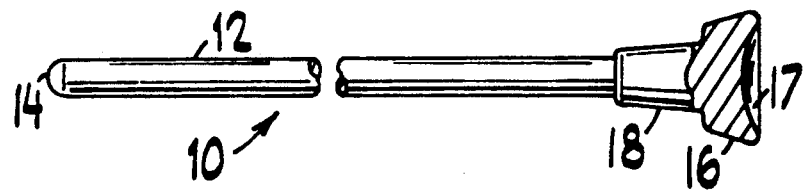
FIG. 11 is a plan view of a cannula introducer or obturator for use with the cannula of FIG. 8, the proximal end of the introducer being partially in cross-section.

With the wrist slightly extended, the proximal edge of the carpal ligament is lifted with an instrument of choice (such as forceps 11) and blunt cannula inserter or obturator 10 (best seen in FIGS. 3 and 11) is introduced into the carpal tunnel. Obturator 10 comprises a cylindrical shaft 12 having a blunt distal tip 14 and a proximal handle portion 16. In FIG. 11 the proximal portion 16 is shown partly in cross-section to disclose a thumb recess 17 molded into the proximal end of the obturator. A tapered shoulder portion 18 is provided between the proximal end of shaft 12 and the distal end of handle 16. In the preferred embodiment, obturator 10 is a single molded piece and shaft 12 has a circular cross-section with a diameter of 4 millimeters and a length of 100 millimeters.

Figure 4:
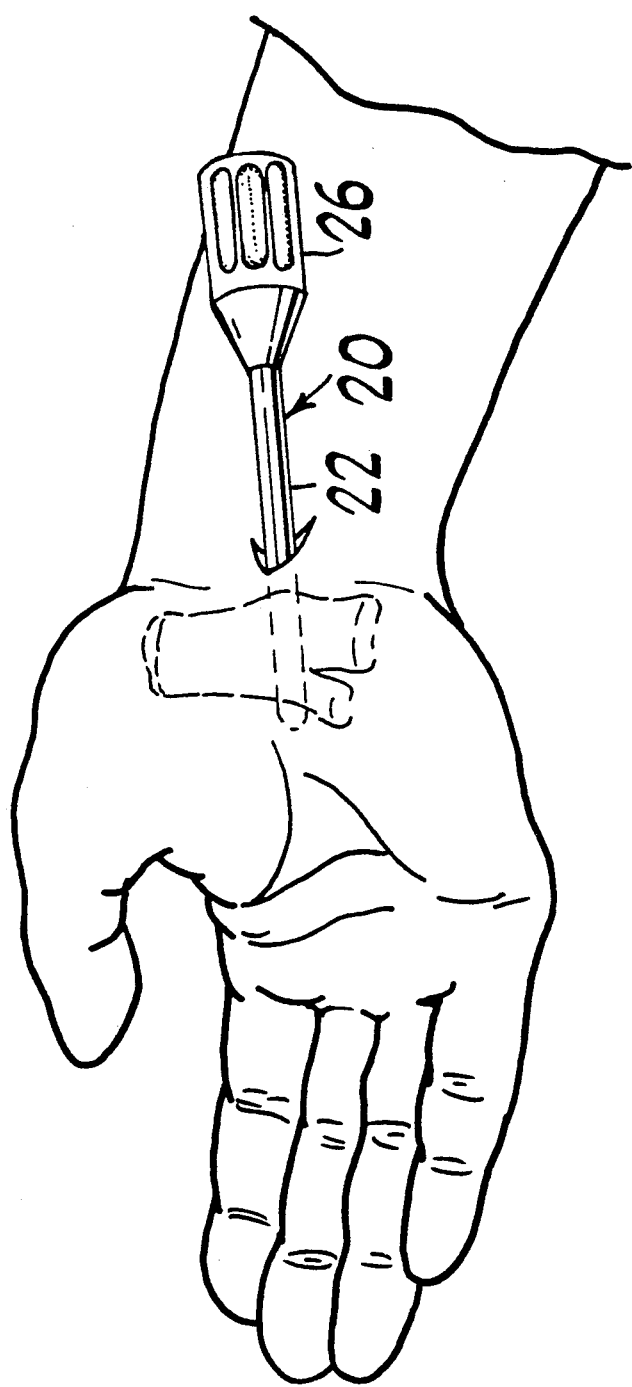
Figure 12:
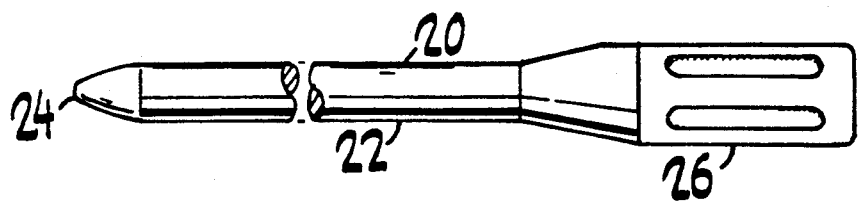
FIG. 12 is a plan view of a dilator for use in the invention.
Figure 13:
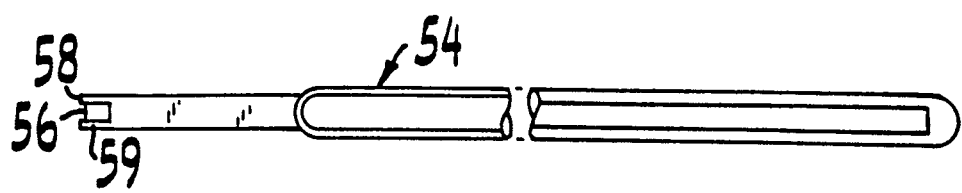
FIG. 13 is a plan view of a knife suitable for use in the procedure which is the subject hereof.
Figure 14:
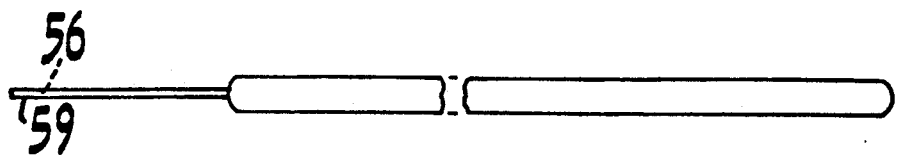
FIG. 14 is a side elevational view of the knife of FIG. 13.
Figure 15:
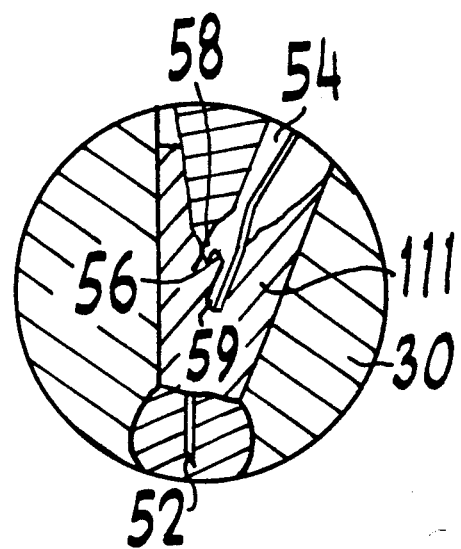
FIG. 15 is a schematic representation of a view of the transverse carpal ligament as seen through an endoscope during a portion of the procedure described herein.

After obturator 10 has been introduced into the carpal tunnel, it is removed and replaced with a dilator 20 (best seen in FIGS. 4 and 12). Dilator 20 has a cylindrical shaft 22 with a relatively blunt distal tip 24 and a proximal handle portion 26. In the preferred embodiment, dilator 20 is also molded as an integral piece with the diameter of shaft 22 equal to 5.5 millimeters and its length equal to 75 millimeters. The overall length of the dilator (approximately 115 millimeters) is made the same as the cannula described below in order to give the surgeon the feel of working with similar instrument lengths as he or she works with different instruments during the course of the procedure.

Progressive dilation of the carpal tunnel continues by removing dilator 20 and inserting another dilator (not shown) having a similar shape and length although a larger shaft diameter. In the preferred embodiment the use of a 5.5 millimeter dilator followed by a 7 millimeter dilator has been satisfactory.

Figure 9:
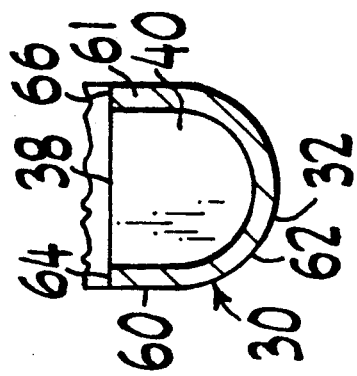
FIG. 9 is a cross-sectional view of FIG. 8 taken along the line 9—9.
Figure 10:
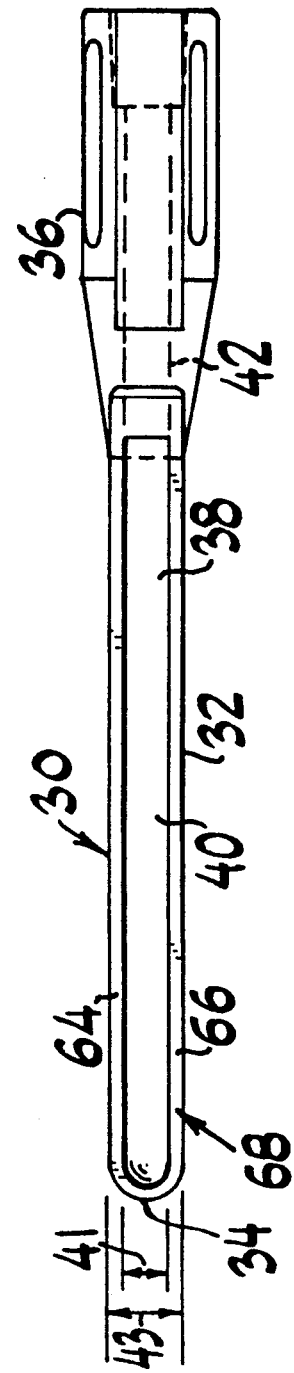
FIG. 10 is a plan view of the cannula shown in FIG. 8.

At this point in the procedure cannula 30 (best seen in FIGS. 5-10) is utilized and it would be helpful to describe the features of cannula 30 before proceeding with the procedural steps of the invention. Cannula 30 comprises an elongated shaft 32, distal tip 34 and proximal handle portion 36. In the preferred embodiment distal tip 34 is closed although it will be understood that apertures necessary or convenient for the injection molding of cannula 30 may be present in distal tip 34 without departing from the scope of the present invention. As best seen in FIGS. 9 and 10, shaft 32 has a top opening 38 extending from distal tip 34 to a point slightly in front of handle portion 36. Opening 38 forms a longitudinal slot or groove 40 and clearly allows full access to the interior of shaft 32 which is also accessible through a longitudinal bore 42 formed along the axis of cannula 30 and through handle portion 36. In the preferred embodiment the internal width 41 of the slot is 4.5 millimeters, the external width 43 of the slot is 7 millimeters and the height 45 of shaft 32 is 6 millimeters. The diameter of bore 42 equals the width of interior 40 and, in the preferred embodiment is made to receive a 4 millimeter arthroscope (without sheath) as will be understood below. The width of interior 40 should be sufficient to enable the chosen arthroscope to slide freely. If it is too wide the surgeon would have to be too concerned about aiming the scope rather than merely following the path of the slot. Having the width of opening 38 equal to interior 40 enables the scope to move upwardly (relative to FIG. 9) as necessary. The proximal end of bore 42 is enlarged to form bore 44 which has a slight taper and is shaped to receive shoulder portion 18 of obturator 10 as will be described during the subsequent steps of the procedure.

Figure 5:
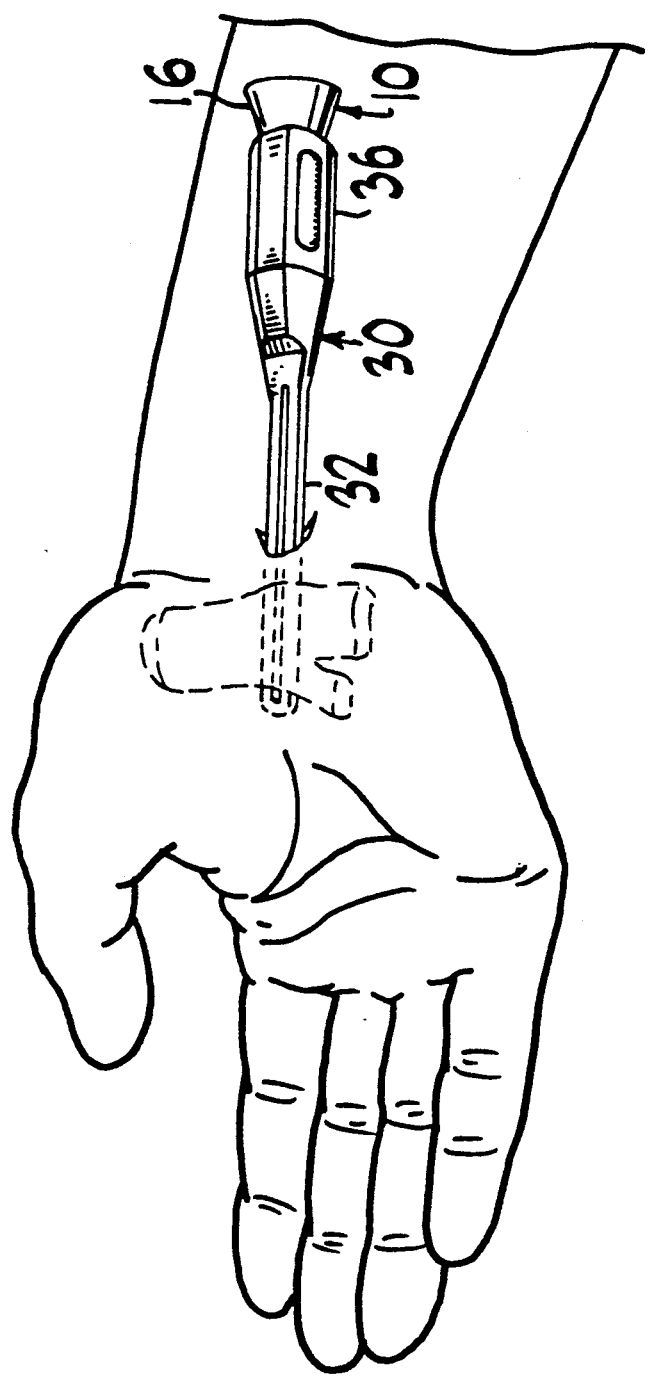
Figure 6:
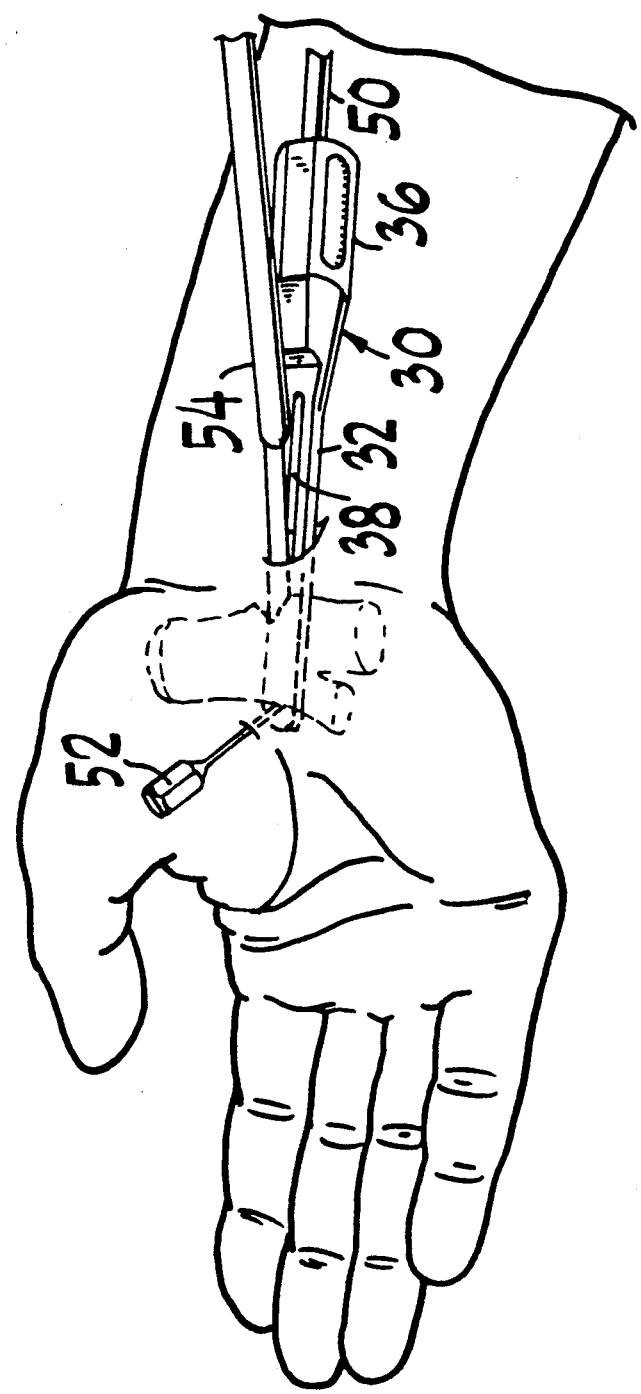
Figure 7:
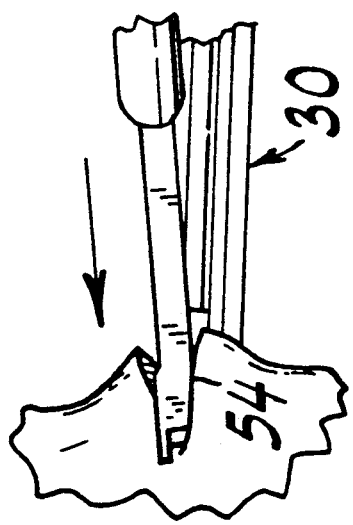
FIG. 7 is a larger scale view of a portion of FIG. 6 showing a knife cutting the transverse carpal ligament.
Figure 8:
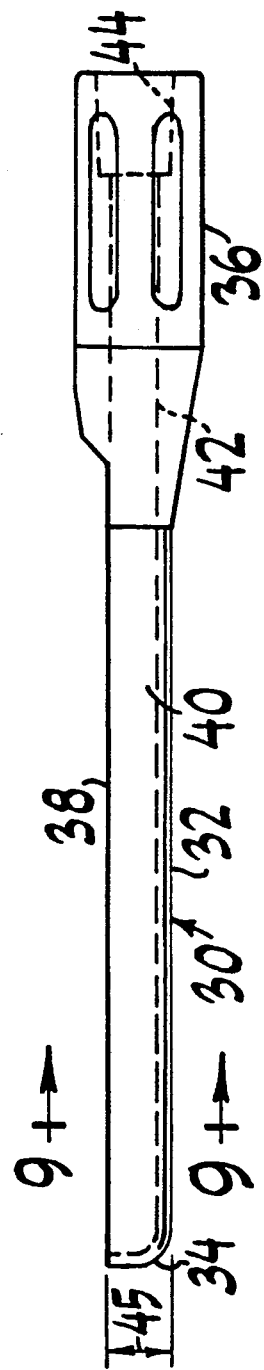
FIG. 8 is a side elevational view of the cannula which is part of the invention described herein.

After the largest diameter dilator is inserted under the carpal ligament and removed, obturator 10 is inserted through the proximal end of cannula 30 until its shoulder 18 seats within bore 44 of the cannula. The obturator and cannula are sized appropriately so that when shoulder 18 is so seated distal tip 14 is either contiguous to or near the interior surface of distal tip 34 and shaft 12 substantially fills the interior of shaft 32. The combined cannula/obturator is then introduced into the carpal tunnel with opening 38 facing upwardly against the bottom of the carpal ligament, as best seen in FIG. 5. The cannula/obturator is inserted until distal tip 34 is approximately at the distal margin of the carpal ligament. At this point it may be helpful to extend the wrist over 2 to 3 folded towels or some other support and press the proximal part of the cannula down in order to stretch the carpal ligament over opening 38. The obturator is then removed and a standard 4 millimeter arthroscope 50 is inserted into the proximal end of cannula 30 through bore 42 and into slot 40. For this surgical application the term "arthroscope" is interchangeable with "endoscope". The arthroscope is positioned within cannula 32 sufficiently to enable the surgeon to view the carpal ligament. It has been found that using an arthroscope with a 30° viewing angle provides a satisfactory field of view for this procedure.

A standard needle 52 (preferably on the order of 25 gauge) is inserted through the palmar skin at the distal border of the transverse carpal ligament and visualized with the endoscope. The needle serves as a mark to prevent the surgeon from inadvertently cutting too deeply into the palm.

Arthroscope 50 is then retracted within slot 40 sufficiently to enable knife 54 to be inserted into slot 40, as best seen in FIGS. 6, 7, 13 and 15. The knife is placed into slot 40 distally to the tip of the arthroscope and its distal cutting edge 56 (set between non-sharpened borders 58 and 59) is engaged on the proximal edge of the transverse carpal ligament while viewing it with the scope, best seen in FIGS. 7 and 15. The transverse carpal ligament is cut by pushing the knife distally under endoscopic control. A characteristic gritty sensation is felt as the ligament is cut and once the distal margin is cut the knife "gives". Using a probe, the cut margins of the ligament should be palpated to ensure that the ligament has been completely divided. The cannula may be turned radially to inspect the median nerve and then removed. The skin is then closed with an appropriate closure and a volar splint is applied for one week.

It will be noted that slot 40 is defined on each longitudinal side by two parallel wall sections 60 and 61 the bottom ends of which are joined by a semi-circular connecting portion 62 (best seen in FIG. 9). The top sides of the parallel wall sections are formed as top surfaces 64 and 66 which together with transverse top surfaces at the distal and proximal ends of the slot form a rim 68 in which all these top surfaces lie in a common plane. When opening 38 is inserted under the carpal ligament, rim 68 serves as a planar tissue or ligament contacting surface and top surfaces 64 and 66 serve to rotationally stabilize cannula 30 and help to maintain opening 38 in the proper orientation under the ligament. This may be considered an automatic orientation feature which facilitates the surgical procedure by eliminating any need for the surgeon to be concerned about properly orienting opening 38 once the cannula is properly placed under the ligament. The natural tension of the ligament tends to keep opening 38 properly oriented.

It will be understood by those skilled in the art that numerous modifications and improvements may be made to the preferred embodiment of the invention disclosed herein without departing from the spirit and scope hereof.

What is claimed is:

1. A device for use in an endoscopic surgical procedure comprising:
a straight, elongated cannula having one closed end, one open end and a longitudinal slot in the surface of said cannula extending from a point adjacent said closed end to a point adjacent said open end, said slot having a D-shaped cross-section extending over substantially the full length thereof, the flat part of said D-shape lying along the rim of said longitudinal slot, said D-shaped cross-section having a predetermined size adapted to receive and guide an instrument inserted axially into the cannula from said open end.

2. A device according to claim wherein the interior surfaces of the longitudinal sides of said slot are transversely and longitudinally parallel over a predetermined portion of their surfaces.

3. A device according to claim 1 wherein said cannula also has a D-shaped exterior cross-section.

4. A device according to claim 1 wherein, in use, said slot is adapted to extend along said cannula from a first point on the interior of a body to a second point exterior to said body.

5. A device according to claim 1 wherein said cannula cross-section comprises:
a first straight wall portion,
a second straight wall portion parallel to and spaced from said first portion, and
a third, substantially semi-circular wall portion connecting one end of said first wall portion to one end of said second wall portion, the radius of curvature of said third portion being substantially equal to one-half the distance between said first and second portions.

6. A device for use in an endoscopic surgical procedure comprising:
an elongated cannula having one closed end, one open end and a longitudinal groove formed in the surface of said cannula and extending form a point adjacent said closed end to a point adjacent said open end, said longitudinal groove having a predetermined size adapted to receive and guide an instrument inserted axially into the cannula from said open end, said cannula provided with a planar tissue contacting surface on each side of said groove, said contacting surfaces adapted to maintain the rim of said longitudinal groove in abutting engagement with selected tissue and to resist rotation of said cannula about its axis.

7. A device according to claim wherein said planar surfaces lie in a common plane.

8. A device according to claim 7 wherein said rim further comprises distal and proximal transverse surfaces contiguous to said planar tissue contacting surfaces and situated at the distal and proximal ends of said groove, respectively.

9. A method for the endoscopic treatment of a portion of the human anatomy comprising:
   inserting through a single incision a cannula having one closed distal end, one open proximal end and a longitudinal slot extending from a point adjacent said closed end to a point adjacent said open end, said slot having a D-shaped cross-section with the flat part of the "D" lying along the rim thereof;
   placing the rim of said longitudinal slot of said cannula adjacent a desired work site;
   inserting an endoscope along the axis of said cannula through the open proximal end of the cannula into a position to view a desired work site adjacent said longitudinal slot of the cannula;
   inserting through said longitudinal slot obliquely to the axis of said cannula and in front of the viewing port of the endoscope an instrument for treatment of the work site adjacent said longitudinal slot.

10. The method of claim further comprising the step of inserting an obturator into said cannula through its proximal open end prior to inserting said cannula through said incision.

11. A method for the endoscopic treatment of a portion of the human anatomy comprising:
    inserting through a single incision a cannula having a longitudinal slot extending from a point adjacent its distal end to a point adjacent its proximal end;
    orienting said longitudinal slot of said cannula adjacent a desired work site;
    inserting an endoscope along the axis of said cannula through the open proximal end of the cannula into a position to view a desired work site adjacent said longitudinal slot of the cannula;
    inserting through said longitudinal slot obliquely to the axis of s id cannula and in front of the viewing port of the endoscope an instrument for treatment of the work site adjacent said longitudinal slot.

12. A method for the endoscopic treatment of an anatomical body comprising:
    inserting through a single incision a cannula having a distal end, an open proximal end and a longitudinal slot extending from a point adjacent said distal end to a point adjacent said proximal end, said slot having a D-shaped cross-section with the flat part of the "D" lying along the rim of said longitudinal slot;
    placing the rim of said longitudinal slot of said cannula adjacent a desired work site;
    inserting an endoscope parallel to the axis of said cannula through the open proximal end of the cannula into a position to view a desired work site adjacent said longitudinal slot of the cannula;
    inserting parallel to the axis of said cannula and in front of the viewing port of the endoscope an instrument for treatment of the work site adjacent said longitudinal slot.

13. An elongated cannula for use in the endoscopic surgical treatment of an endoscopic work site comprising:
    a hollow cylindrical body having a distal end and a proximal end, said proximal end provided with an opening for receiving therethrough at least one instrument for placement in the interior of said hollow cylindrical body; and
    a longitudinal slot; and
    tissue contacting means for contacting tissue at the endoscopic work site to thereby enable said slot to be maintained in a predetermined stable position relative to the endoscopic work site, said tissue contacting means comprising spaced and longitudinally parallel surfaces along the opening of said slot, said surfaces lying in a common plane parallel to the axis of said cannula.

* * * * *